(12) United States Patent
Piantoni et al.

(10) Patent No.: US 9,084,697 B2
(45) Date of Patent: Jul. 21, 2015

(54) DEVICE AND A METHOD FOR MAKING ABSORBENT PADS USED IN PERSONAL SANITARY ITEMS

(75) Inventors: Matteo Piantoni, Albino (IT); Luca Pedretti, Crema (IT)

(73) Assignee: GDM S.p.A. (IT)

( * ) Notice: Subject to any disclaimer, the term of this patent is extended or adjusted under 35 U.S.C. 154(b) by 402 days.

(21) Appl. No.: 13/254,135

(22) PCT Filed: Mar. 9, 2010
(Under 37 CFR 1.47)

(86) PCT No.: PCT/IB2010/051001
§ 371 (c)(1),
(2), (4) Date: Feb. 16, 2012

(87) PCT Pub. No.: WO2010/103457
PCT Pub. Date: Sep. 16, 2010

(65) Prior Publication Data
US 2012/0145314 A1    Jun. 14, 2012

(30) Foreign Application Priority Data
Mar. 9, 2009 (IT) .............................. BO2009A0138

(51) Int. Cl.
*A61F 13/15* (2006.01)
*A61F 13/49* (2006.01)
(Continued)

(52) U.S. Cl.
CPC ........... *A61F 13/15764* (2013.01); *A61F 13/15* (2013.01); *A61F 13/15577* (2013.01);
(Continued)

(58) Field of Classification Search
CPC . A61F 13/15577; A61F 13/53; A61F 13/539; A61F 13/15; A61F 13/49; B32B 37/00; B32B 38/0004; Y10T 156/1069; Y10T 156/1074; Y10T 156/1077; Y10T 156/1087; Y10T 156/1097; Y10T 156/1098
USPC ......... 156/260, 263, 264, 270, 271, 259, 265, 156/301, 303, 300, 302; 428/102, 107
See application file for complete search history.

(56) References Cited

U.S. PATENT DOCUMENTS 1,584,450 A * 5/1926 Hager ............................ 156/259
5,484,505 A * 1/1996 Isakson et al. ................. 156/470
(Continued)

FOREIGN PATENT DOCUMENTS

DE       4335919       4/1995
EP       1820757       8/2007
(Continued)

OTHER PUBLICATIONS

Perkins, Kathryn: Stamp with Style, 4 pages, 1998.*
(Continued)

*Primary Examiner* — Linda L Gray
(74) *Attorney, Agent, or Firm* — Timothy J. Klima; Shuttleworth & Ingersoll, PLC (57) ABSTRACT

Absorbent pads for personal sanitary items are made by a device that comprises a set of pick-up heads (2) moving along a feed path (P), a first application unit (5) and a second application unit (6) by which a respective first portion (4a) and second portion (4b) of an absorbent pad are placed on the pick-up head (2), and a motion-inducing mechanism, coupled to the pick-up head (2), which is designed to bring about a relative displacement between the first portion (4a) and the second portion (4b), so that when the second portion (4b) is placed over the first portion (4a), the one will be covered by the other only in part. A method of making absorbent pads using the device in question includes the steps of preparing a first portion (4a) and a second portion (4b) of an absorbent pad, then placing the second portion (4b) over the first portion (4a) in such a way that the first portion (4a) is covered only in part by the second portion (4b).

15 Claims, 5 Drawing Sheets

(51) Int. Cl.
*A61F 13/53* (2006.01)
*A61F 13/539* (2006.01)
*B32B 37/00* (2006.01)

(52) U.S. Cl.
CPC ................ *A61F13/49* (2013.01); *A61F 13/53* (2013.01); *A61F 13/539* (2013.01); *B32B 37/00* (2013.01); *Y10T 156/1062* (2015.01); *Y10T 156/1069* (2015.01); *Y10T 156/1074* (2015.01); *Y10T 156/1077* (2015.01); *Y10T 156/1087* (2015.01); *Y10T 156/1097* (2015.01); *Y10T 156/1098* (2015.01)

(56) References Cited

U.S. PATENT DOCUMENTS

| | | |
|---|---|---|
| 6,165,306 A | 12/2000 | Rajala |
| 6,527,902 B1 | 3/2003 | Rajala |
| 2001/0016245 A1* | 8/2001 | Tuman et al. ................ 428/99 |
| 2002/0092604 A1* | 7/2002 | McCabe et al. ............. 156/202 |
| 2003/0121614 A1 | 7/2003 | Tabor et al. |
| 2004/0245069 A1 | 12/2004 | Hook et al. |
| 2005/0167874 A1* | 8/2005 | Larsson et al. ............. 264/122 |
| 2008/0196564 A1 | 8/2008 | McCabe |
| 2010/0030175 A1 | 2/2010 | Konawa |
| 2011/0174430 A1* | 7/2011 | Zhao et al. ................. 156/207 |

FOREIGN PATENT DOCUMENTS

| | | |
|---|---|---|
| FR | 2690843 | 11/1993 |
| WO | 2008/010752 | 1/2008 |
| WO | 2008/078805 | 7/2008 |

OTHER PUBLICATIONS

International Search Report and Written Opinion dated Aug. 16, 2010 from PCT application.

* cited by examiner

DEVICE AND A METHOD FOR MAKING ABSORBENT PADS USED IN PERSONAL SANITARY ITEMS

This application is the National Phase of International Application PCT/IB2010/051001 filed Mar. 9, 2010 which designated the U.S. and that International Application was published under PCT Article 21(2) in English.

This application claims priority to Italian Patent Application No. BO2009A000138 filed Mar. 9, 2009 and PCT Application No. PCT/IB2010/051001 filed Mar. 9, 2010, which applications are incorporated by reference herein.

TECHNICAL FIELD

The present invention relates to a device and a method for making absorbent pads as incorporated into personal sanitary items, and to a machine for manufacturing personal sanitary items, equipped with such a device.

The invention finds application, to advantage, in the manufacture of personal sanitary products having a high absorbent capacity, such as nappies (diapers) for babies, incontinence pads for adults, and the like.

BACKGROUND ART

Conventionally, the manufacture of such products involves preparing an absorbent pad that will be sandwiched normally between a permeable inner layer of non-woven fabric and an impermeable outer layer of polyethylene.

In the case of nappies and incontinence pads (baby and adult diapers), the pad consists in a mass of cellulose fibres that is suitably shaped and preformed, then interposed between the two aforementioned layers.

More exactly, devices of conventional type for making the pads in question utilize bands of compacted cellulose wound previously into rolls. These bands of material are fed to suitable grinding means by which the compacted cellulose is broken down into an incoherent mass of cellulose fibres, or fluff.

The fibres generated in this way are conveyed toward aspirating cavities negatively reproducing the required shape of the pad, and held together with the aid of aspirating means by which a partial vacuum is created in the selfsame cavities.

The shape of the aspirating cavities is dictated by the fact that the pads of the baby and adult sanitary items in question must present an exact geometry. In these products, more exactly, the central portion of the pad must have an absorbent capacity distinctly higher than that of the peripheral portion. Accordingly, the pads must be fashioned in such a manner that the central portion will be much thicker than the peripheral portion.

Once the pad has been prepared in this way, it is placed between the inner and outer layers.

Disadvantageously, the devices and the methods employed hitherto to make the pads in question are decidedly complex, and do not always deliver correct and dependable results.

In effect, preparation of the pads by the method described above involves holding together an incoherent mass of fibres that tend easily to scatter, with the result that the shape of the pad is lost.

This creates significant problems, deriving both from the notable amount of fluff dust produced, and the fact that considerable precautions are needed to keep the pad stable.

Furthermore, it is not unusual for the aspirating cavities to be filled either incompletely or erratically during the process of forming the pads, with a considerable number of defective items consequently having to be discarded.

Prior art methods of manufacturing other related items, such as sanitary napkins for women, now include the use of pads prepared from bands of an already formed and stable absorbent material, wound into rolls. In this instance the pads are prepared by cutting portions of the required shape from the continuous band.

However, the bands in question are of constant thickness and this precludes their use in the manufacture of nappies for babies and incontinence pads for adults, as they cannot guarantee a correct differentiation between the absorbent capacities at the centre and at the periphery of the pad.

DISCLOSURE OF THE INVENTION

Accordingly, the object of the present invention is to provide a device and a method for making absorbent pads used in personal sanitary items, also a machine for manufacturing personal sanitary items comprising such a device, in which the drawbacks associated with the prior art as described above are overcome.

One object of the present invention, in particular, is to provide a device and a method for making absorbent pads used in personal sanitary items, also a machine for manufacturing personal sanitary items comprising the device, by which the absorbent pads can be made quickly and conveniently.

A further object of the present invention is to provide a device and a method for making absorbent pads used in personal sanitary items, also a machine for manufacturing personal sanitary items comprising the device, such as will significantly reduce the incidence of rejects in production.

The stated objects are substantially realized in a device for making absorbent pads used in personal sanitary items as described herein, also in a machine for manufacturing personal sanitary items comprising such a device as described herein, and in a method for making absorbent pads used in personal sanitary items as described herein.

BRIEF DESCRIPTION OF THE DRAWINGS

The invention will now be described in detail, by way of example, with the aid of the accompanying drawings, in which.

DETAILED DESCRIPTION OF THE PREFERRED EMBODIMENTS OF THE INVENTION

In the accompanying drawings, numeral 1 denotes a device according to the invention, in its entirety, for making absorbent pads as used in personal sanitary items, in particular nappies (known also as diapers) for babies and/or incontinence products for adults.

The device 1, as will become clearer in the course of the present description, comprises at least one pick-up head 2 in receipt of a first discrete portion 4a and a second discrete portion 4b combining to make up an absorbent pad 4 for personal sanitary items.

The first and second portions 4a and 4b of the pad 4 are made using a continuous absorbent material, prepared previously and stable, which is wound into rolls or onto reels.

The absorbent material might also be treated previously with chemical additives serving to increase its absorbent capacity.

Figure 1:
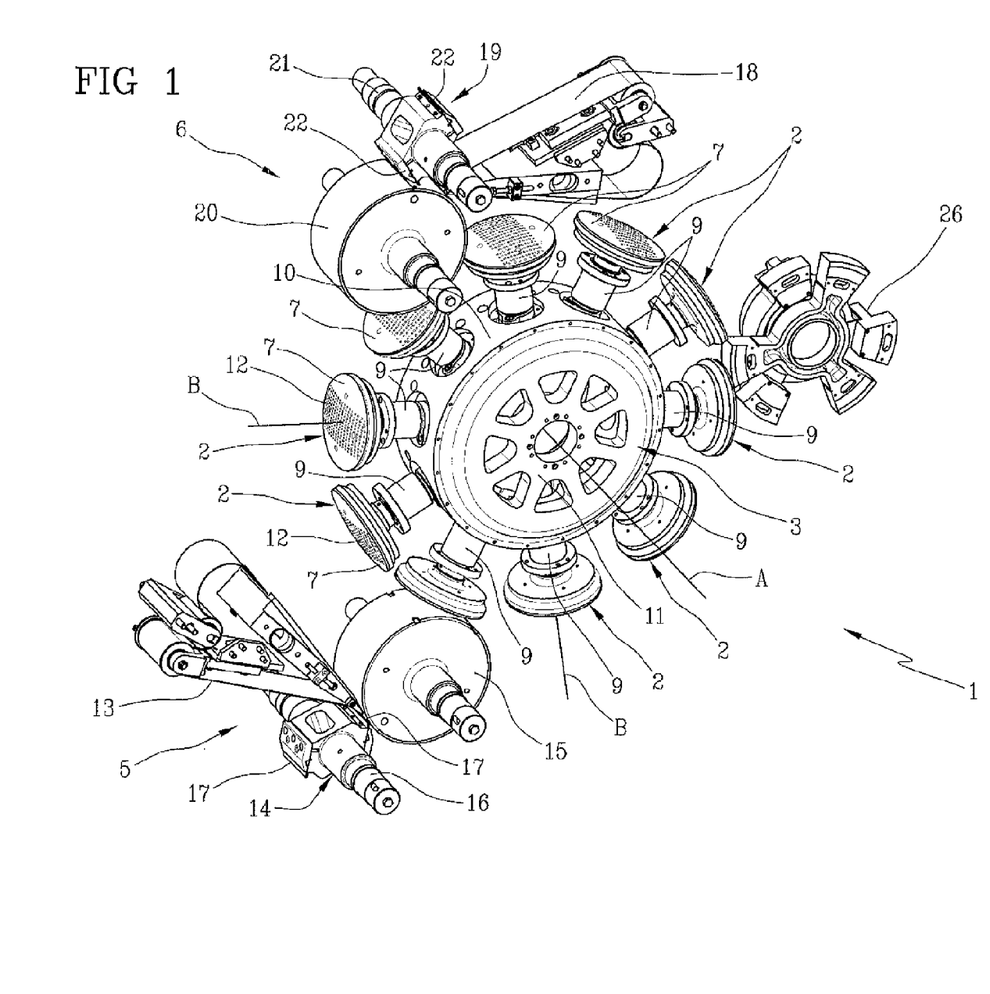
FIG. 1 shows a device according to the present invention for making absorbent pads incorporated into personal sanitary items, illustrated in perspective.
Figure 2:
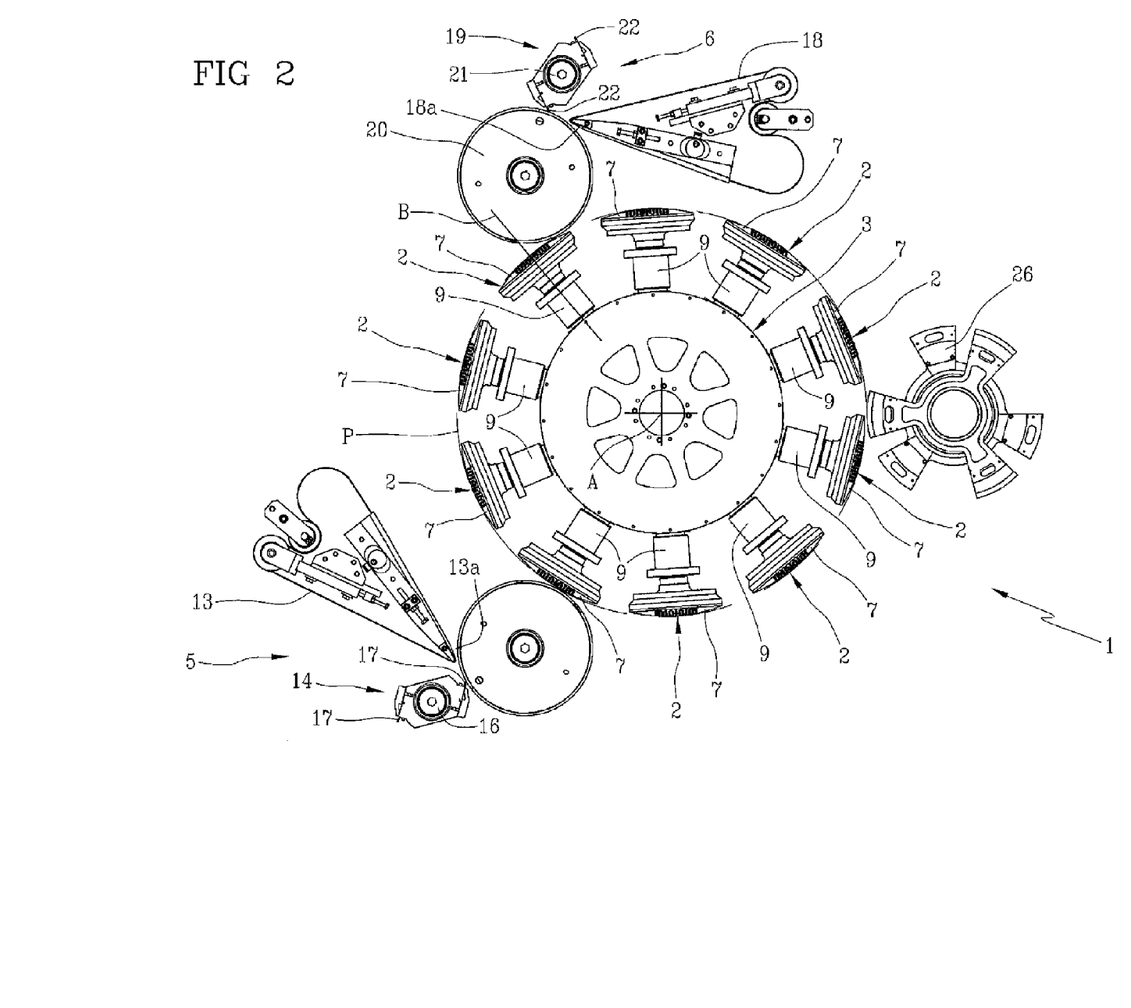
FIG. 2 is a side view of the device illustrated in FIG. 1.

The pick-up head 2 is capable of movement along a feed path P, preferably circular (FIG. 2), and to this end the device 1 further comprises a drum 3, rotatable about a central axis of rotation A, with which the pick-up head 2 is associated.

To advantage, the device 1 comprises a plurality of pick-up heads 2 associated with the drum 3 and, preferably, equispaced angularly about the periphery of the selfsame drum 3.

The device 1 further comprises a first application unit 5 by which the first portions 4a of the pads 4 are prepared and placed in succession on the pick-up heads 2, and a second application unit 6 by which the second portions 4b of the pads 4 are prepared and placed in succession on the pick-up heads 2, each positioned over a relative first portion 4a.

In the embodiment described thus far, the first application unit 5 is similar in every respect to the second application unit 6, both being positioned adjacent to the drum 3 and to the pick-up heads 2, and in particular, located each in a position substantially tangential to the aforementioned feed path P.

As illustrated in the drawings, the second application unit 6 occupies a position downstream of the first application unit 5, relative to the feed path P followed by the pick-up heads 2.

The device 1 further comprises motion-inducing means operating on the pick-up heads 2 and/or on the first application unit 5 and/or on the second application unit 6, designed to bring about a relative displacement of the first portion 4a and the second portion 4b in such a way that the second portion 4b will cover the first portion 4a only in part.

In short, the effect produced on the two portions 4a and 4b of the pad 4 by the motion-inducing means, directly or indirectly, is to position the selfsame portions 4a and 4b skew one relative to another.

Adopting this method, a central part of the pad 4 consists of the two portions 4a and 4b, mutually superposed, whilst a peripheral part consists either of the first portion 4a only, or the second portion 4b only. Self-evidently, this means that the central part of the pad 4 is substantially double the thickness of the peripheral part and therefore possesses a greater absorbent capacity than the selfsame peripheral part.

In the embodiment described thus far, the pick-up heads 2 are rotatable each about a respective axis of rotation B, and engaged actively by the motion-inducing means in such a way as will cause them to rotate thus through a predetermined angle.

As discernible in the drawings, the single axis of rotation B extends transversely to the feed path P. In effect, the axis of rotation B of each pick-up head 2 is disposed substantially transverse to the axis of rotation A of the drum 3, and more precisely, the axes of rotation B of all the pick-up heads 2 radiate substantially perpendicular to the axis of rotation A of the drum 3.

In practice, the motion-inducing means actively engage the pick-up heads 2 at least when the heads are located between the first application unit 5 and the second application unit 6.

In operation, as each pick-up head 2 moves along the feed path P, revolving about the centre axis of rotation A of the drum 3, it will pass adjacent to the first application unit 5 and receive the first portion 4a of the pad 4 from this same unit.

Advancing subsequently toward the second application unit 6, this same pick-up head 2 is caused to pivot on its axis of rotation B through the predetermined angle aforementioned.

In this way, when the pick-up head 2 in question reaches the second application unit 6, the second portion 4b of the pad 4 will be positioned over the first portion 4a, but only in part, the latter portion having been rotated through the predetermined angle aforementioned.

Figure 3:
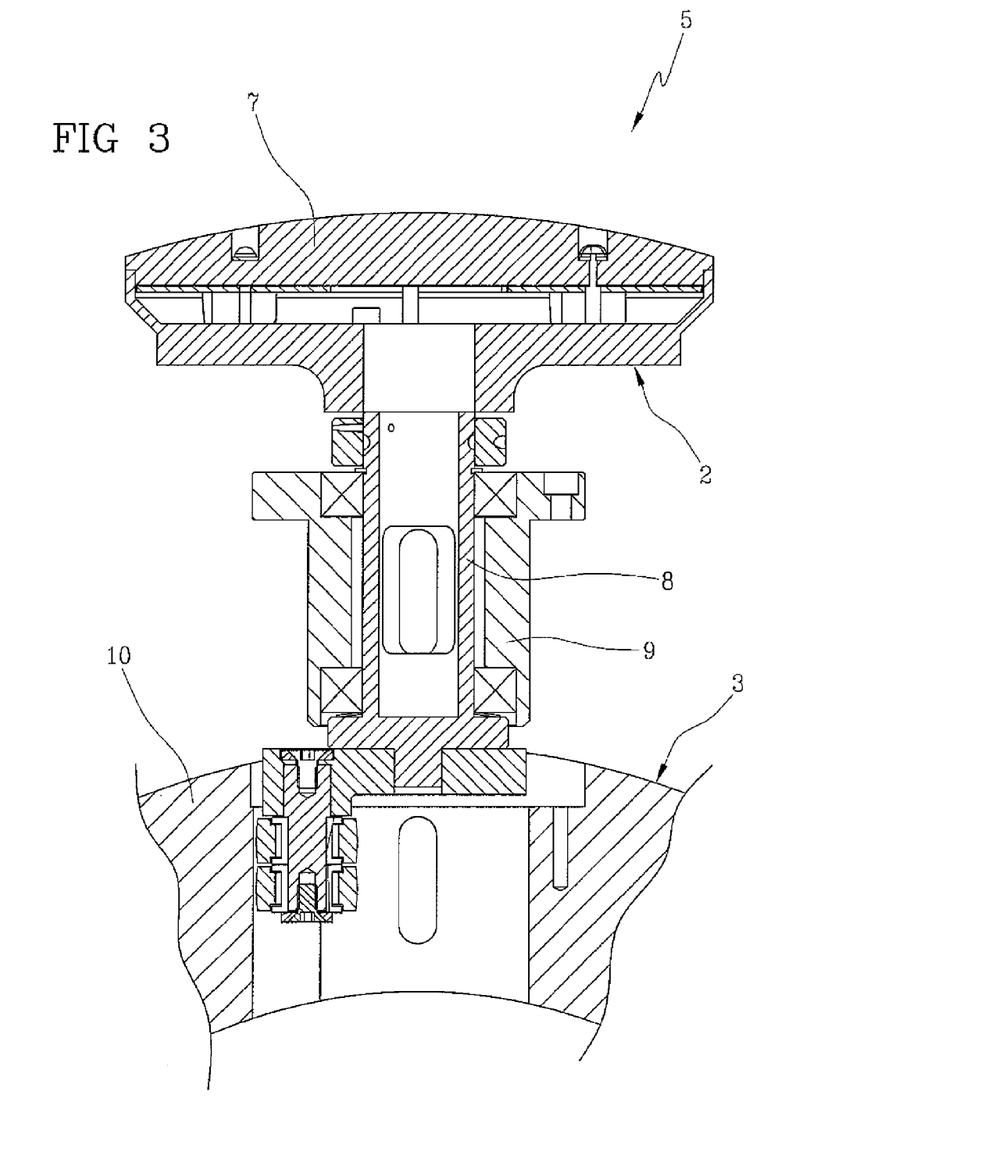
FIG. 3 shows a detail of the device of FIG. 1, viewed from the side and in section.

As illustrated to advantage in FIG. 3, each pick-up head 2 comprises a carrier element 7 on which the portions 4a and 4b of the pad 4 are placed, and a rotatable shaft 8 connected to the carrier element 7 in such a way that angular motion can be induced in the selfsame element as described above. The rotatable shaft 8 is connected to the motion-inducing means (not illustrated in the drawings), and each pick-up head 2 further comprises a sleeve 9 associated rigidly with the drum 3 by means of threaded fasteners (not illustrated); the shaft 8 is inserted through and aligned concentrically with the sleeve 9.

The drum 3 presents a cylindrical wall 10, to which the pick-up heads 2 are attached, and a base wall 11 connected to the cylindrical wall 10. Thus, the cylindrical wall 10 and the base wall 11 combine to delimit a space internally of which the motion-inducing means are advantageously accommodated, at least in part.

By way of example, the motion-inducing means comprise a cam-follower profile (not illustrated), and a cam (not illustrated) associated with the pick-up heads 2, such as will allow the selfsame pick-up heads 2 to be rotated selectively depending on their angular position relative to the central axis of rotation A of the drum 3.

The device 1 further comprises vacuum means operating at least via the pick-up heads 2 and serving to retain the portions 4a and 4b of the pad 4 on the heads.

The vacuum means comprise a system (not illustrated) such as will generate an aspirating air flow. The carrier element 7 of the single pick-up head 2 presents a plurality of through holes 12 through which the aspirating air flow is generated. To this end, the rotatable shaft 8 of each head is hollow, and thus able to admit and convey the aspirating air flow generated through the carrier element 7.

In the example illustrated, the carrier element 7 of each pick-up head 2 presents a substantially convex, and preferably spherical profile. To advantage, this type of geometry allows the portions 4a and 4b of the pad to be placed more easily and precisely on the head. Moreover, this same feature is conducive to greater precision in the step of distancing the pad 4 formed on each pick-up head 2.

The first application unit 5 comprises a belt conveyor 13 serving to transport a continuous strip of absorbent material decoiled from a roll positioned upstream.

Located at one end 13a of the conveyor 13 is a cutter mechanism 14 by which the first portions 4a of successive pads 4 are cut and released to a transfer roller 15.

In greater detail, the cutter mechanism 14 comprises a rotating shaft 16 and a plurality of blades 17, rigidly associated with and set in rotation by the shaft 16. The rotating blades 17 are caused to strike against the transfer roller 15 and cut through the strip.

Preferably, at least the conveyor 13 and the transfer roller 15 will be vacuum components. The transfer roller 15 rotates substantially tangential to the feed path P and is designed to accelerate the portions 4a along the feed path, distancing them one from the next.

Similarly, the second application unit 6 comprises a belt conveyor 18 serving to transport a continuous strip of absorbent material decoiled from a roll positioned upstream.

Located at one end 18a of the conveyor 18 is a cutter mechanism 19 by which the second portions 4b of successive pads 4 are cut and released to a transfer roller 20.

In greater detail, the cutter mechanism 19 comprises a rotating shaft 21 and a plurality of blades 22, rigidly associated with and set in rotation by the shaft 21. The rotating blades 22 are caused to strike against the transfer roller 20 and cut through the strip.

Preferably, at least the conveyor 18 and the transfer roller 20 will be vacuum components. The transfer roller 20 rotates substantially tangential to the feed path P and is designed to accelerate the portions 4b along the feed path, distancing them one from the next.

The continuous strips from which the first portions 4a and the second portions 4b of the pads 4 are cut can be decoiled from separate rolls.

In the example illustrated, conversely, the two strips are obtained from a single band of absorbent material that is cut longitudinally to generate the single strips.

Figure 4:
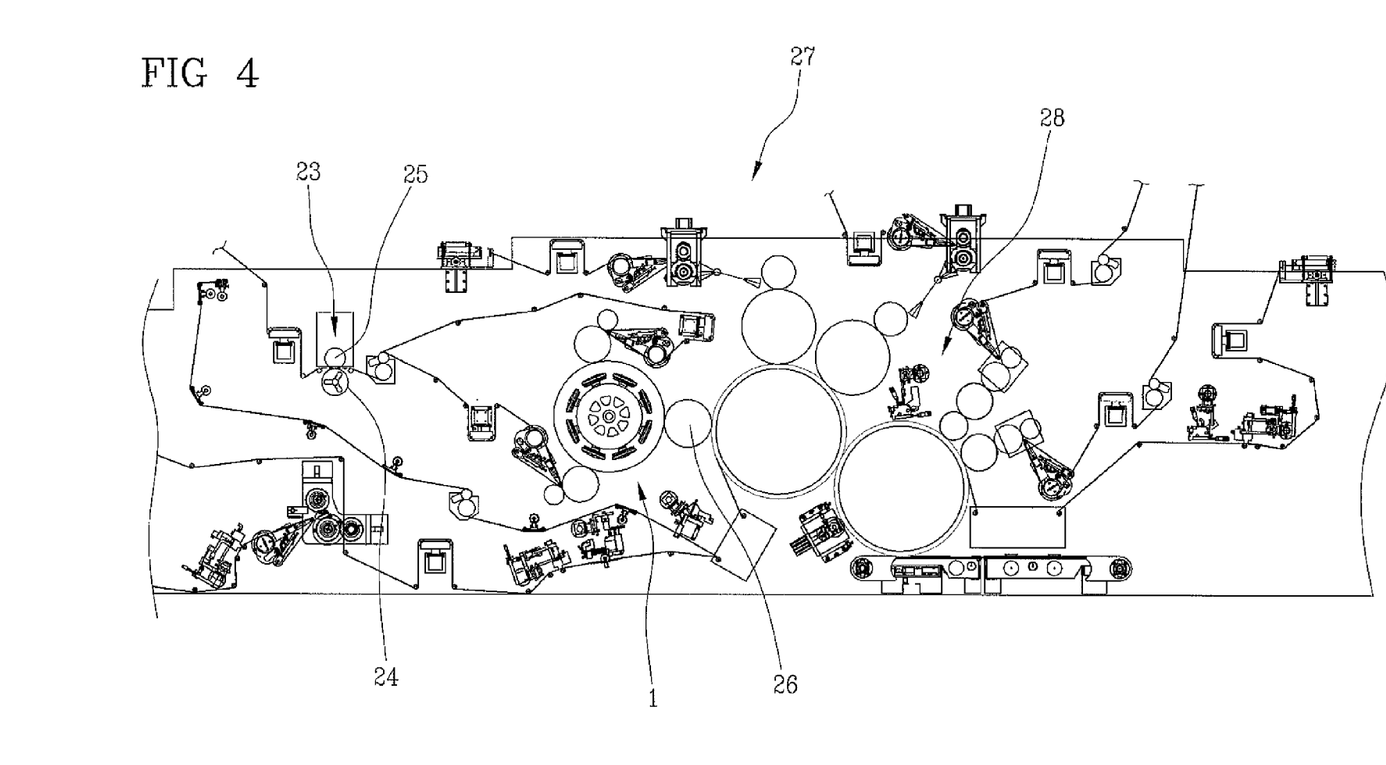
FIG. 4 shows a machine for manufacturing personal sanitary items comprising the device of FIG. 1, illustrated in a schematic side elevation view.

To this end, the device 1 further comprises cutter means 23 by which the continuous band of absorbent material is taken up at an infeed station and cut longitudinally in a direction coinciding substantially with the lengthwise direction of the band (FIG. 4).

The cutter means 23 are positioned upstream both of the first application unit 5 and of the second application unit 6, and comprise a rotating disc type blade 24 interacting with an anvil roller 25. The band of absorbent material is fed to the cutter means 23 between the blade 24 and the anvil roller 25.

The device 1 further comprises an unloading unit 26 by which pads 4 formed on the pick-up heads 2 are distanced from the selfsame heads 2. The unit 26 in question is positioned substantially tangential to the feed path P at a point downstream of the second application unit 6.

In greater detail, the pads 4 formed on the pick-up heads 2 are taken up by the unloading unit 26, accelerated, and released onto strip of material such as polyethylene, used in the manufacture of nappies or incontinence pads (baby or adult diapers).

As illustrated in FIG. 4, the invention relates also to a machine 27 used to manufacture personal sanitary items, typically nappies for babies and/or incontinence pads for adults.

The machine 27 comprises at least one device 1 for making absorbent pads incorporated into personal sanitary items as described above, and means 28 by which the sanitary items are formed and assembled.

The invention relates also to a method of making absorbent pads used in personal sanitary items, typically nappies for babies and/or incontinence pads for adults.

Figure 5:
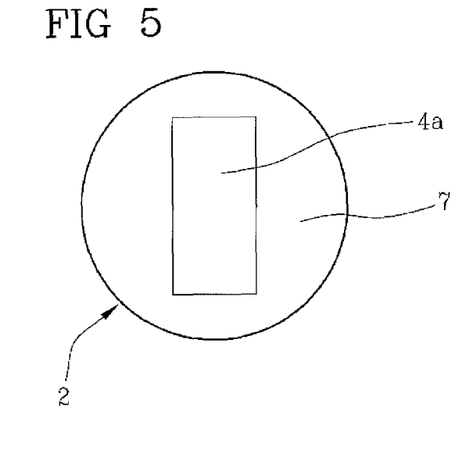
FIGS. 5 to 8 show a detail of the device in FIG. 1, illustrated schematically in a succession of operating steps.

The method includes an initial step of preparing the first portion 4a of the pad 4 (FIG. 5), and similarly, a parallel step of preparing the second portion 4b of the pad 4.

The first portion 4a is rotated (FIG. 6), and the prepared second portion 4b thereupon placed over the first portion 4a (FIG. 7), at least in part.

More exactly, the method comprises a step of shifting or angling the first portion 4a relative to the second portion 4b, in such a way that the second portion 4b will cover the first portion 4a in part only.

An alternative version of the method might include a step of shifting or angling the second portion 4b relative to the first portion 4a.

Needless to say, the step of placing the second portion occurs only after the first portion has been shifted.

Once the step of positioning the second portion 4b has been concluded, with the first portion 4a covered in part, the pad 4 is formed.

Adopting the method disclosed, a central part of the pad 4 consists of the two superposed portions 4a and 4b, whereas a peripheral part consists either of the first portion 4a only, or the second portion 4b only. Self-evidently, this means that the central part of the pad 4 is substantially double the thickness of the peripheral part and therefore possesses a greater absorbent capacity than the peripheral part.

Figure 6:
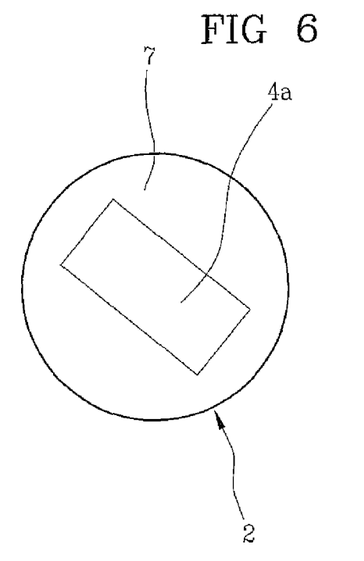
Figure 7:
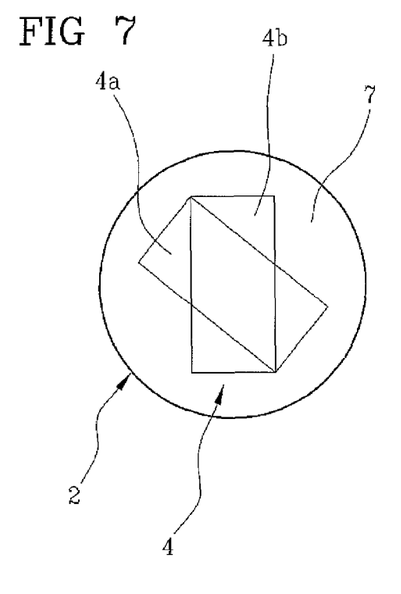

In the preferred embodiment illustrated, the step of shifting the first portion 4a is accomplished by rotating the selfsame portion 4a (FIG. 6).

More exactly, the step in question is accomplished by rotating the first portion 4a about a central axis substantially perpendicular to a plane occupied by the selfsame first portion 4a.

Figure 8:
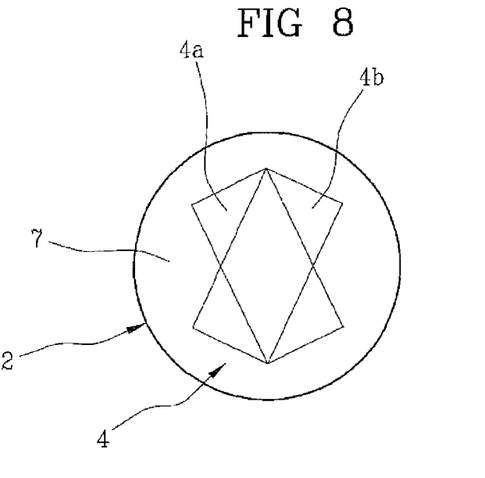

Finally, the pad 4 prepared in this way is rotated again, this time into symmetrical alignment with the sanitary item in production (FIG. 8).

The step of preparing the first portion 4a of the pad 4 includes the steps of preparing a respective continuous strip of absorbent material and cutting the continuous strip repeatedly so as to generate a succession of discrete first portions 4a. The cutting step is implemented preferably by severing the continuous strip transversely to its lengthwise direction.

Similarly, the step of preparing the second portion 4b of the pad 4 includes the steps of preparing a respective continuous strip of absorbent material and cutting the continuous strip repeatedly so as to generate a succession of discrete second portions 4b. The cutting step is implemented preferably by severing the relative strip transversely to its lengthwise direction.

Advantageously, the step of preparing the strips includes the step of preparing a continuous band of absorbent material and cutting this same continuous band along a direction substantially parallel to a lengthwise direction of the band, so as to generate the two distinct strips.

The stated objects are achieved by the invention, which affords significant advantages.

Adopting the device and the method described above, in effect, the pads can be made simply and swiftly by joining two portions of absorbent material in such a way that one partially superposes the other, thereby creating a central portion of absorbent capacity greater than that presented by a peripheral portion of the single pad.

In short, pads suitable for babies' nappies (diapers) or adult incontinence pads can be created swiftly and simply, avoiding the use of incoherent and volatile fluff material with its associated handling difficulties.

Moreover, precisely by reason of the extreme simplicity achieved, the number of defective or unsuitable items produced is significantly reduced, with obvious advantages from a production and economic standpoint.

The invention claimed is:

1. A method for making an absorbent core assembly for a personal sanitary item, comprising:

preparing a discrete absorbent first portion of an absorbent core assembly for a personal sanitary item, wherein the personal sanitary item is at least one chosen from a diaper and an incontinence pad and the absorbent core assembly is assembled with at least one further outer layer to form the personal sanitary item;

preparing a discrete absorbent second portion of the absorbent core assembly;

each of the first portion and the second portion having a length suitable for the personal sanitary item;

placing the second portion over the first portion such that the first portion is covered in part by the second portion to form the absorbent core assembly;

displacing at least one chosen from the first portion and the second portion before placing the second portion over the first portion;

wherein the displacing is accomplished by rotating the at least one chosen from the first portion and the second portion to provide an orientation of the first portion with respect to an orientation of the second portion whereby the first portion is misaligned with respect to the second portion such that, after the second portion is placed over the first portion, each one of the first portion and the second portion is covered only partially by the other of the first portion and the second portion.

2. The method as in claim 1, wherein the rotating the first portion is accomplished by inducing rotational movement about a central axis substantially perpendicular to a plane occupied by the first portion.

3. The method as in claim 1, wherein, the preparing of at least one chosen from the first portion and the second portion includes preparing strips of absorbent material and cutting the strips to obtain the at least one chosen from the first portion and the second portion.

4. The method as in claim 3, wherein the preparing the strips includes preparing a continuous band of absorbent material and cutting the continuous band of absorbent material along a direction substantially parallel to a lengthwise direction of the continuous band of absorbent material to divide the continuous band of absorbent material into the strips.

5. The method as in claim 4, wherein the cutting the continuous band into the strips is accomplished by cutting the strips along a direction substantially transverse to a lengthwise direction of the strips.

6. The method as in claim 3, wherein the cutting the continuous band into the strips is accomplished by cutting the strips along a direction substantially transverse to a lengthwise direction of the strips.

7. The method as in claim 1, wherein a central part of the absorbent core assembly consists of two superposed portions defined by the first portion and the second portion, and a peripheral part of the absorbent core assembly consists of a first peripheral portion consisting of only the first portion and a second peripheral portion consisting of only the second portion so that the central part of the absorbent core assembly is double a thickness of the peripheral part.

8. The method as in claim 1, wherein the step of placing the second portion over the first portion occurs only after the first portion has been rotated.

9. The method as in claim 7, and further comprising transferring the absorbent core assembly onto a continuous web of material used to manufacture the personal sanitary item.

10. The method as in claim 9, wherein the first portion and the second portion are of a substantially same length.

11. The method as in claim 10, wherein the first portion has a pair of opposing faces of area greater than areas of other faces of the first portion and the first portion is rotated by inducing rotational movement about a line substantially perpendicular to at least one of the pair of opposing faces.

12. The method as in claim 9, wherein the first portion has a pair of opposing faces of area greater than areas of other faces of the first portion and the first portion is rotated by inducing rotational movement about a line substantially perpendicular to at least one of the pair of opposing faces.

13. The method as in claim 1, wherein the first portion has a pair of opposing faces of area greater than areas of other faces of the first portion and the first portion is rotated by inducing rotational movement about a line substantially perpendicular to at least one of the pair of opposing faces.

14. The method as in claim 1, wherein the first portion and the second portion are of a substantially same length.

15. The method as in claim 1, and further comprising transferring the absorbent core assembly onto a continuous web of material used to manufacture the personal sanitary item.

* * * * *